United States Patent [19]

Babler

[11] Patent Number: 4,567,265
[45] Date of Patent: Jan. 28, 1986

[54] CYCLOPROPANOID CYANOESTERS AND METHOD OF MAKING SAME

[75] Inventor: James H. Babler, Evanston, Ill.

[73] Assignee: Loyola University of Chicago, Chicago, Ill.

[21] Appl. No.: 570,874

[22] Filed: Jan. 16, 1984

[51] Int. Cl.$^4$ ............... C07C 120/00; C07C 121/46; C07D 213/127; C07D 211/26
[52] U.S. Cl. .................... 546/16; 546/330; 548/469; 548/560; 549/13; 549/76; 549/331; 549/496
[58] Field of Search .............. 260/464, 465 D; 546/230, 330, 16; 549/76, 496, 331, 13; 548/560, 469

[56] References Cited

U.S. PATENT DOCUMENTS

| | | | |
|---|---|---|---|
| 3,962,053 | 6/1976 | Kornblum | 260/464 X |
| 4,118,412 | 10/1978 | Cleare et al. | 260/464 |
| 4,276,225 | 6/1981 | Lantzsch et al. | 260/464 X |
| 4,284,582 | 8/1981 | Kaye et al. | 260/464 |

OTHER PUBLICATIONS

Fieser, et al., Reagents for Organic Synthesis (1967), vol. 1, pp. 515 and 1252.
Fieser, et al., Reagents for Organic Synthesis (1975), vol. 5, p. 685.
Fieser, et al., Reagents for Organic Synthesis (1981), vol. 9, pp. 323-324.
Annen, et al., Chem. Ber., 111, pp. 3094-3104, (1978).

Primary Examiner—Joseph Paul Brust
Attorney, Agent, or Firm—Marshall, O'Toole, Gerstein, Murray & Bicknell

[57] ABSTRACT

Cyclopropanoid cyanoesters of the formula:

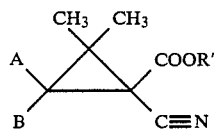

where R' is —CH$_3$ or —CH$_2$CH$_3$, and A is
(a) —H, or
(b) A, B represents an aliphatic group joined to a carbon atom on the cyclopropanoid ring, thereby forming a spiro group, A, B being selected from structures having the formula:
(i) —(CH$_2$)$_n$—, wherein n=3, 4, or 5, and
(ii) —(CH$_2$)$_2$—Y—(CH$_2$)$_2$—, wherein Y is NCH$_3$, O, or S); and, when A is —H, B is selected from the group consisting of:

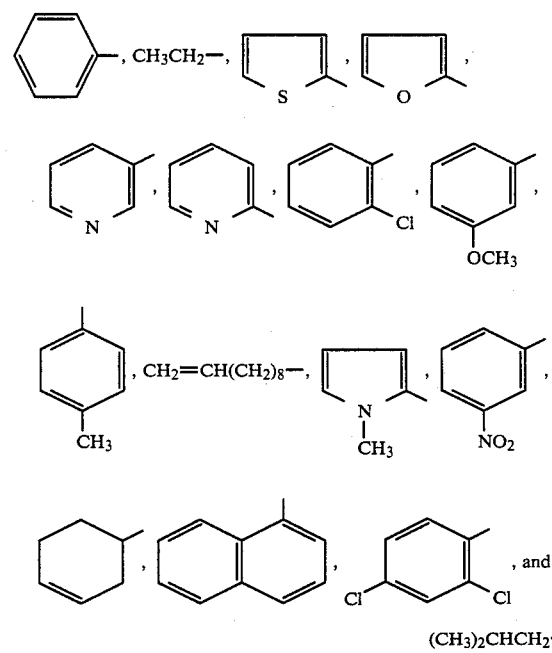

(CH$_3$)$_2$CHCH$_2$—.

are disclosed. These compositions are useful in the synthesis of pyrethroids. A process for synthesis of cyclopropanoid cyanoesters by reacting 2-nitropropane with cyanoesters of the general formula:

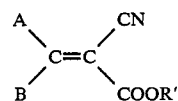

is also disclosed and claimed.

9 Claims, No Drawings

CYCLOPROPANOID CYANOESTERS AND METHOD OF MAKING SAME

BACKGROUND OF THE INVENTION (1) Field of the Invention

The present invention relates to novel cyclopropanoid compositions useful in the synthesis of pyrethroids and to methods of preparing these compositions. The compounds of the invention have the structure

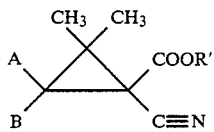

where R' is —CH$_3$ or —CH$_2$CH$_3$ and A is either —H or A, B represents a group having a carbon atom in common with the cyclopropanoid ring, the A, B group having the formula —(CH$_2$)$_n$— (n=3, 4, or 5) or —(CH$_2$)$_2$—Y—(CH$_2$)$_2$— (Y=NCH$_3$, O, or S). When A is —H, B is selected from the group consisting of:

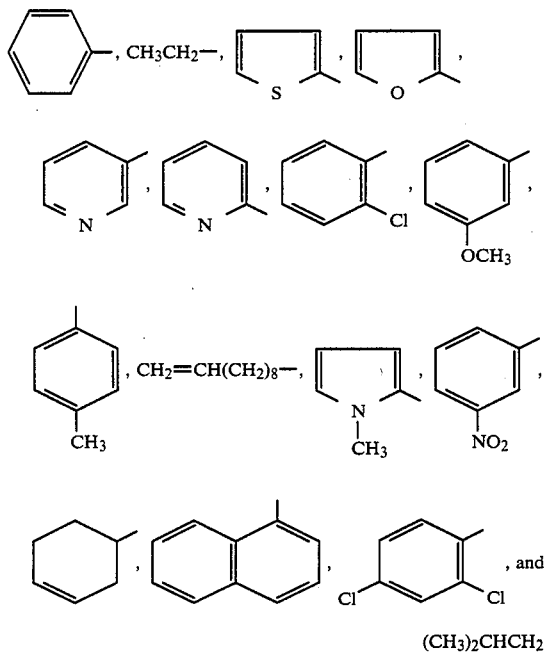

(CH$_3$)$_2$CHCH$_2$—.

In accordance with the method of the present invention, these compounds, as well as other pyrethroid intermediates, can be manufactured from aldehydes in a two step process:

Step 1:

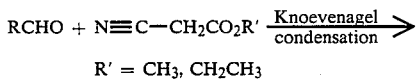

R' = CH$_3$, CH$_2$CH$_3$

Step 2:

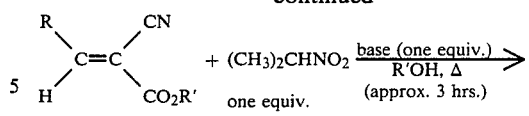

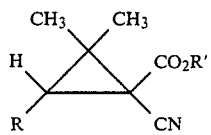

70-95% yield

Alicyclic ketones of the formula RR"CO, wherein R,R"=—(CH$_2$)$_n$—(n=3, 4, or 5) or R,R"=—(CH$_2$)$_2$—Y—(CH$_2$)$_2$—(Y=NCH$_3$, O, or S), can also be used as starting materials in lieu of the aldehyde (RCHO).

Although the experimental conditions for a Knoevenagel condensation vary from one starting compound to the next, one can examine the literature for the exact procedure to be followed for a given starting material. An excellent and lengthy review [including a list of various aldehydes and ketones which have been successfully condensed with methyl or ethyl cyanoacetate (listed in Table VII of the review)] can be found in *Organic Reactions*, 15, pp. 204–599 (1967).

(2) Description of the Prior Art

Because of their low mammalian toxicity, high insecticidal activity, and biodegradability, the pyrethroids have proved quite useful for the control of insect pests. A study of the literature reveals that in the past decade various routes have been developed for the synthesis of these compounds. A collection of a number of methods of preparing certain ester derivatives of trans-chrysanthemic acid and the related synthetic pyrethroids can be found in "Synthetic Pyrethroids", ACS Symposium Series 42, M. Elliott, Ed., American Chemical Society, Washington, D.C., 1977, pp. 45–54, 116–136; and, "The Total Synthesis of Natural Products", Vol. 2, J. ApSimon, Ed., Wiley, New York, 1973, pp. 49–58. A survey of a number of syntheses of pyrethroid acids is reported in *Angewandte Chemie, Internat. Ed. Engl.*, 20, 703–722 (1981).

Of particular interest to the present application are the methods disclosed by Krief et al. and by Annen et al.

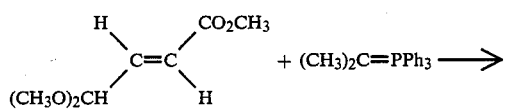

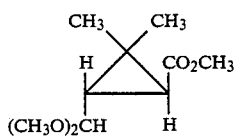

Reference: A. Krief, DOS 2,615,160 (1976), Roussel-Uclaf; M. J. Devos, L. Hevesi, P. Bayet, and A. Krief, *Tetrahedron Lett.*, 3911 (1976).

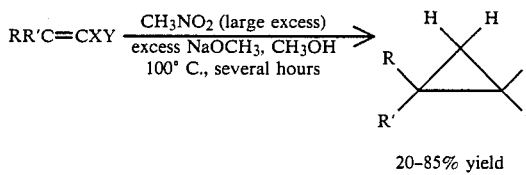

20-85% yield

X, Y = CN, CO₂R''

Reference: K. Annen, et al, *Chem. Ber.* 111. 3094–3104 (1978).

The Krief et al. process utilizes a phosphorane [(CH$_3$)$_2$C=PPh$_3$] to generate a three-membered ring. Phosphorane reagents are very costly and require one equivalent of a strong base such as n-butyllithium to generate. In addition, phosphoranes must be synthesized in the absence of air and protic solvents (even traces of moisture rapidly destroy them); and therefore this type of process is highly unsuitable for an industrial scale-up. Moreover, the Krief cyclization yields a product which can be used to prepare the acid component of only trans pyrethroids whereas, as illustrated below, the method of the present invention results in either the cis-stereoisomer [which often exhibits greater insecticidal activity—e.g., See: M. Elliott, A. W. Farnum, N. F. Janes, P. H. Needham, and D. A. Pulman, *Pesticide Sci.*, 6, 537 (1975)], or the trans stereoisomer. More significantly, Krief et al. utilized their cyclization with only a few specific compounds, such as those having the structure RCH=CHCO$_2$R'. In sharp contrast, the method of the present invention failed to yield any cyclopropanoids using RCH=CHCO$_2$R' (R=CH$_3$ or C$_6$H$_5$) and (CH$_3$)$_2$CHNO$_2$(2-nitropropane) in the presence of base in refluxing alcohol.

Annen et al., utilizes a nitro compound and unsaturated cyanoesters similar to those used in the method of the present invention in order to generate cyclopropanoids. However, these are many significant differences between the Annen et al. procedure and the present method:

Annen's cyclization step, which is preceded by a Michael reaction, utilizes a nitro leaving group bonded to a primary (1°) carbon:

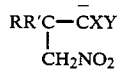

The intermediate formed by the Michael reaction in the method of the present invention has the leaving group at a tertiary (3°) center:

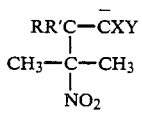

Due chiefly to steric factors, one would expect the ring closure of this latter structure to be much less favorable (if it proceeds at all) than for the similar process involving Annen's (1°) structure. Any basic textbook in organic chemistry indicates that nucleophilic substitution at a 1° carbon is much faster than at a 3° center. For example, the reaction of CH$_3$CH$_2$Br with I$^\ominus$ is 1,000 times faster than that between (CH$_3$)$_3$C—Br and I$^\ominus$. [Reference: Morrison and Boyd, "Organic Chemistry," 3rd Edition, p. 465]. Indeed, the major reaction pathway when nucleophiles interact with 3° halides is often elimination (to yield an alkene) rather than substitution [Reference: Morrison and Boyd, "Organic Chemistry," 3rd Ed., p. 485].

Nothwithstanding these theoretical considerations, the cyclization reaction of the present invention proceeds under considerably milder conditions than those employed by Annen et al. Annen employs metal alcohol at 100° C. (which requires a pressure reactor since the boiling point of CH$_3$OH is 65° C.) and excess base accompanied by a very large excess of nitromethane. The method of the present invention procedes readily at 65° C. (refluxing methanol) or 78° C. (refluxing ethanol) and requires only a stoichiometric quantity of base and 2-nitropropane.

Annen et al. shows that his procedure was used successfully to convert

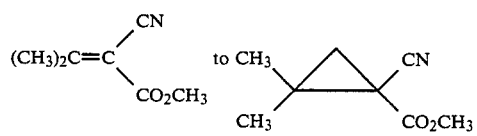

in 19% yield. The cyclizatin method of the present invention, using (CH$_3$)$_2$CHNO$_2$, failed when applied to

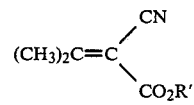

(R'=CH$_3$ or CH$_2$CH$_3$). The fact that this failure is not simply due to the steric factors involved in forming a fully-substituted ring is illustrated by the fact that a sterically complex cyclopropanoid was formed readily (in less than 5 hours) and in high yield (greater than 70%) using the method of the present invention:

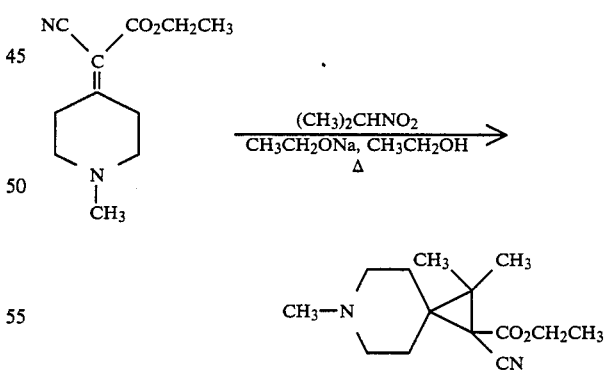

It appears that the process of Annen et al. is most successful when applied to complex steroidal systems and gives poor yields when applied to relatively simple systems. The method disclosed herein, in contrast, proceeds readily in 70-95% yields with a variety of substrates, both simple and complex.

BRIEF DESCRIPTION OF THE INVENTION

As stated previously, the present invention discloses a series of novel cyclopropanoid compositions together with methods of preparing these compositions and related compounds. The compounds of the invention have the structure:

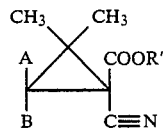

where R' is methyl or ethyl and A is either hydrogen or A and B together represent a group having a carbon atom in common with the cyclopropanoid ring and having the formula —$(CH_2)_n$— (n=3, 4, or 5) or —$(CH_2)_2$—Y—$(CH_2)_2$ where (Y=$NCH_3$, O or S). Two such spirocyclic compounds are ethyl 1'-cyano-3',3'-dimethyl-spiro(4-methyl-4-azacyclohexane-1,2'-cyclopropane)-1'-carboxylate and ethyl 1'-cyano-3',3'-dimethyl-spiro(cyclopentane-1,2'-cyclopropane)-1'-carboxylate

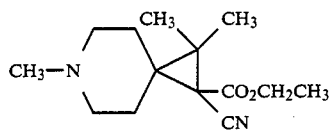

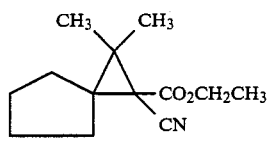

When A and B are not part of such a spiro group, A is —H and B can be any of the following alkyl or aryl substituents: phenyl, ethyl, (2'-thienyl), (2'-furyl), (3'-pyridyl), (2'-pyridyl), o-chlorophenyl, m-methoxyphenyl, p-tolyl, (9'-decen-1'-yl), (1'-methyl-2'-pyrrolyl), m-nitrophenyl, (3'-cyclohexen-1'-yl), 1'-naphthyl; 2',4'-dichlorophenyl; and isobutyl.

With an aldehyde or alicyclic ketone starting material, the products of the invention can be generated in a two-step procedure:

Step 1:

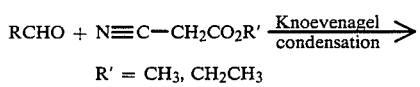

R' = $CH_3$, $CH_2CH_3$ (other simple alkyl groups would be satisfactory as well)

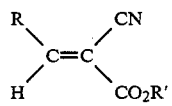

That these products are stereochemically homogeneous can be seen by NMR analysis (only one type of vinyl H is observed).

Step 2:

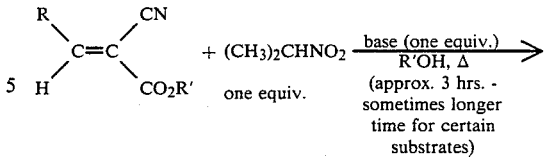

70–95% yield

The base utilized in the Step 2 reaction can be an alkali metal alkoxide such as sodium methoxide or sodium ethoxide.

Examination by NMR revealed the cyclopropanoid products of the present invention to be formed as a single stereoisomer (neglecting optical isomerism)—one which after decarbalkoxylation could be a useful precursor to the acid component of cis-pyrethroids.

The aldehyde starting materials (RCHO) which can be utilized in the Step 1 reaction include those wherein R is an alkyl group containing between 1 and 10 carbon atoms inclusive. For example, the compound

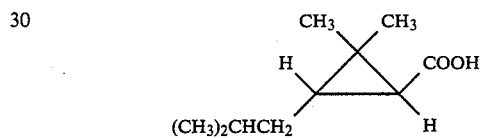

has been reported to give insecticidally-active esters [Drabek et al., DOS 2731033 (1978)], suggesting that R=isobutyl would be a desirable starting material.

Other satisfactory aldehydes include those wherein R is naphthyl, phenyl, or a benzenoid ring substituted at various positions with alkyl, halogen, nitro, or alkoxy substituents—provided that at least *one* of the *ortho* carbons of the benzene ring is substituted with a hydrogen atom (e.g., use of ethyl 2-cyano-3-(2',6'dichlorophenyl)-2-propenoate as a starting material resulted in an insignificant amount of (<10%) of a cyclopropanoid product). Alicyclic rings, including those possessing unsaturation (e.g. 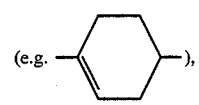 ), and heterocyclic residues possessing N, O, and/or S atoms in the ring—such as furan, thiophene, pyridine, pyrrole, and indole heterocyclic residues—can also be utilized.

Particularly useful aldehydes include benzaldehyde, propionaldehyde, 2-thiophenecarboxyaldehyde, 2-furaldehyde, 3-pyridinecarboxaldehyde, 2-pyridinecarboxaldehyde, o-chlorobenzaldehyde, m-methoxybenzaldehyde, p-tolualdehyde, 10-undecenal, N-methylpyrrole-2-carboxaldehyde (proceeds very slowly), m-nitrobenzaldehyde, 3-cyclohexenecarboxaldehyde, 1-naphthaldehyde, 2,4-dichlorobenzaldehyde, and isovaleraldehyde.

Although a wide range of $C_1$ to $C_{10}$ alkyl groups can be employed, it has been found that aliphatic alpha, beta-unsaturated aldehydes are not useful starting materials.

Ketones of the formula

can be utilized as starting materials in the Knoevenagel (Step 1) reaction. However, with the exception of alicyclic ketones the cyclization step proceeds very poorly, presumably for steric reasons. For example, attempts to form cyclopropanoid products from

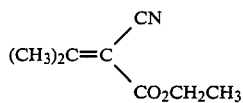

resulted in ~10% crude yield of a mixture of products after reaction times of either 2 or 8 hours at reflux.

Attempts to form cyclopropanoid products from

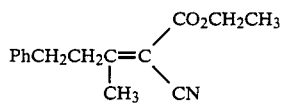

afforded after 2½ hours at reflux the following results: greater than 30% of the product mixture was a non-distillable resinous material; the distilled product (less than 70% yield) contained 20% 4-phenyl-2-butanone and 60% starting cyanoester—the remainder of the distillate could be cyclopropanoid, but was not fully characterized. Longer reaction times merely gave more non-distillable resinous material. In cyclization attempts using

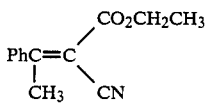

after 3½ hours at reflux, greater than 50% of the product isolated was non-distillable resinous material and the distillate contained mainly (at least one-half) starting material, along with ~20% acetophenone

and other unidentified impurities.

Interestingly enough alicyclic ketones such as cyclopentanone and 1-methyl-4-piperidone could be successfully used to prepare, respectively,

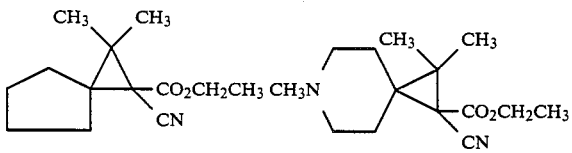

The cyclization reaction to prepare the latter (heterocyclic) compound was complete in approximately 5 hours in refluxing ethanol, whereas the similar reaction involved in the preparation of the former was much slower—being ~50% complete after 6 hours in refluxing ethanol.

Alicyclic compounds useful in the reaction have the formulae $RR''C=O$, where R, $R''=-(CH_2)_n-$ (n=3, 4, or 5), or $R,R''=-(CH_2)_2-Y-(CH_2)_2-$ (Y=O, $NCH_3$, or S).

The novel method of the present invention comprises the Step 2 cyclization reaction, i.e., the reaction of a cyanoester with 2-nitropropane in the presence of an alkoxide base

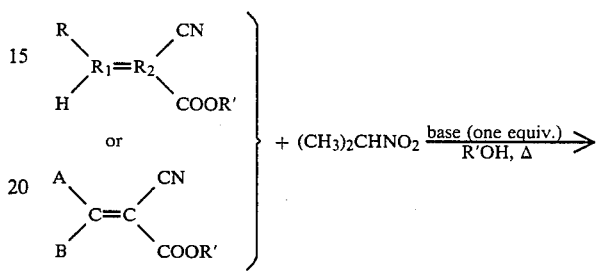

wherein $R_1$ and $R_2$ are carbon, R' is methyl or ethyl, A and B represent a group having the formula $-(CH_2)_n-$ or $-(CH_2)_2-Y-(CH_2)_2-$, n=3, 4, or 5, Y is $NCH_3$, O, or S, and R can be selected from the group consisting of alkyl, haloalkyl, alkenyl, haloalkenyl, cycloalkyl, carboalkoxy, heterocycles possessing N, S, and/or O atoms, cycloalkyl, cycloalkenyl, phenyl and substituted phenyl, bicycloalkyl, phenylalkyl, hydroxyalkyl, aminoalkyl, and thioalkyl, provided that when R is alkenyl, R is not conjugated with $R_1$ and $R_2$, and when R is a substituted phenyl group, at least one of the ortho carbons of said phenyl group is bonded to hydrogen.

The base utilized can be an alkali metal alkoxide such as sodium methoxide or sodium ethoxide, or it can be an alkali metal carbonate such as sodium carbonate or potassium carbonate. Indeed, any base that can dissolve in alcohol to generate a small amount of alkoxide should be suitable for this reaction. The solvent (R'OH) is preferably methyl alcohol or ethyl alcohol, although other simple alcohols would be equally useful (e.g., n-propyl or isopropyl alcohol).

The reaction proceeds in refluxing alcohol solvent. Under these conditions and in order to achieve optimum yields, reaction times in excess of two hours are preferred, depending on the nature of the reactants. For example, the cyclization reaction involving

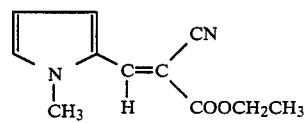

proceeded very slowly (requiring two days in refluxing ethanol), but resulted in a satisfactory product.

In order to prepare the desired acid component of pyrethroids, the cyclopropane-cyanoester is first converted to a nitrile product by means of either of the following methods:

Method A:

-continued

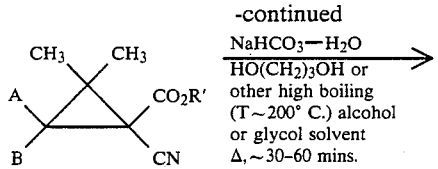
NaHCO₃—H₂O / HO(CH₂)₃OH or other high boiling (T~200° C.) alcohol or glycol solvent
Δ, ~30-60 mins.

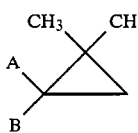

Method B:

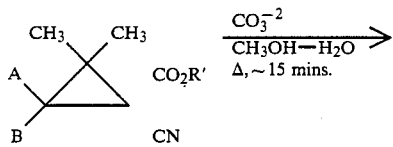
CO₃⁻² / CH₃OH—H₂O
Δ, ~15 mins.

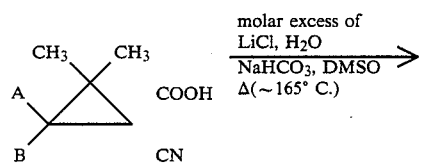
molar excess of LiCl, H₂O / NaHCO₃, DMSO
Δ(~165° C.)

(after acidification of the reaction mixture)

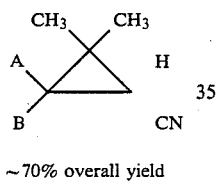

~70% overall yield

It has been found (for A=H, B=C₆H₅) that some (~10-15%) ring-opened material is generated in the one-step process, Method A. Method B (the two-step procedure) is generally preferred in that little or no such ring-opened materials are formed. Another two-step method which could be employed for the conversion is a saponification-decarboxylation process similar to Method B, but employing bicarbonate and 1,3-propanediol at reflux for the second step.

DETAILED DESCRIPTION

The following examples illustrate in greater detail the practice of the present invention, more specifically:

(A) the formation of several intermediate compounds of the formula

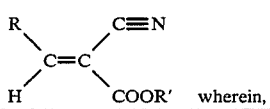
wherein,

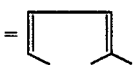

| | |
|---|---|
| 1, R = C₆H₅; R' = CH₂CH₃ | Example I |
| 2, R = C₆H₅; R' = CH₃ | Example II |
| | Example III |
| 3, R =  ; R' = CH₂CH₃ | |

-continued

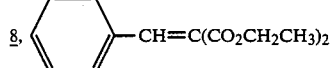
wherein,

| | |
|---|---|
| 4, R = 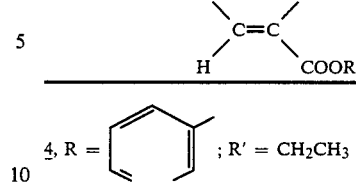 ; R' = CH₂CH₃ | Example IV |
| 5, R = (CH₃)₂CHCH₂—; R' = CH₂CH₃ | Example V |
| 6, R = 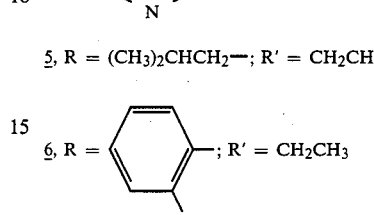 ; R' = CH₂CH₃ | Example X |
| 7, R = 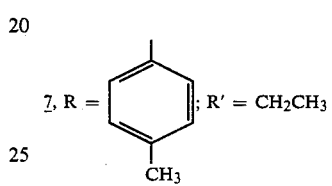 ; R' = CH₂CH₃ | Example XIII |

(B) the formation of intermediates

| | |
|---|---|
| 8, 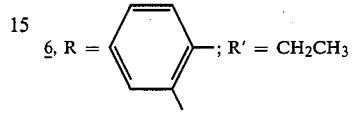—CH=C(CO₂CH₂CH₃)₂ | Example VI |
| 9 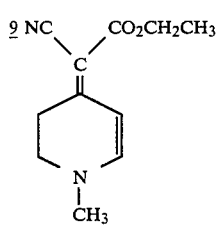 | Example VII |

(C) the formation of cyclopropanoids of the formula

| | |
|---|---|
| 10, R = C₆H₅; R' = CH₂CH₃ | Example VIII |
| 11, R = C₆H₅; R' = CH₃ | Example IX |
| 12, R = 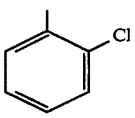 ; R' = CH₂CH₃ | Example X |
| 13, R =  ; R' = CH₂CH₃ | Example XI |
| 14, R = (CH₃)₂CHCH₂—; R' = CH₂CH₃ | Example XII |

-continued

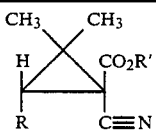

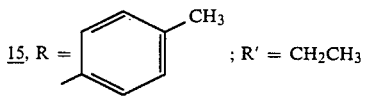    Example XIII

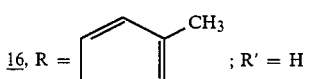    Example XVII (D) the formation of cyclopropanoids of the formula

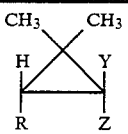

| | |
|---|---|
| 17, R = C₆H₅; Y,Z = CN,H (mixtures of stereoisomers) | Examples XIV & XVI |
| 18, R = C₆H₅; Y = COOH; Z = CN | Example XV |
| | Example XVII |
| 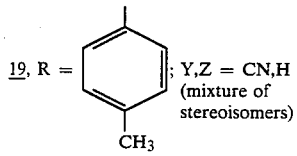 19, R = ; Y,Z = CN,H (mixture of stereoisomers) | |

(E) the formation of

20

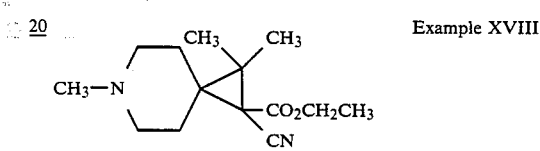    Example XVIII

EXAMPLE I

Preparation of (E)-Ethyl 2-Cyano-3-phenyl-2-propenoate (1)

A mixture containing 4.0 mL (37.6 mmoles) of ethyl cyanoacetate, 3.95 g (37.2 mmoles) of benzaldehyde, 20 mg of β-alanine, and 1.00 mL of glacial acetic acid in 35 mL of benzene was heated at reflux for 3 hours with continuous azeotropic removal of water by means of a Dean-Stark trap. The product was isolated by cooling the mixture to room temperature, pouring it into 75 mL of 2:1 (v/v)1M aqueous NaOH:saturated brine, and extraction with ether. The organic extracts were washed with 75 mL of 2:1 (v/v) 1M aqueous NaOH:saturated brine, 10% aqueous sodium chloride solution, then were dried over anhydrous magnesium sulfate and subsequently filtered. Removal of the ether and benzene by evaporation at reduced pressure afforded 6.88 g (92% yield) of crystalline cyanoester 1: mp 49°–50° C.

EXAMPLE II

Preparation of (E)-Methyl 2-Cyano-3-phenyl-2-propenoate (2)

A mixture containing 2.0 mL (22.7 mmoles) of methyl cyanoacetate, 2.38 g (22.4 mmoles) of benzaldehyde, 18 mg of β-alanine, and 1.00 mL of glacial acetic acid in 35 mL of benzene was heated at reflux for 2 hours with continuous azeotropic removal of water by means of a Dean-Stark trap. The product was isolated as described in the procedure of Example I, affording 3.83 g (91% yield) of crystalline cyanoester 2: mp 90°–91° C.

EXAMPLE III

Preparation of (E)-Ethyl 2-Cyano-3-(2'-thienyl)-2-propenoate (3)

To a solution of 1.052 g (9.38 mmoles) of distilled 2-thiophenecarboxaldehyde (commercially available: Aldrich Chemical Co.) and 1.00 mL (9.4 mmoles) of ethyl cyanoacetate in 3.0 mL of dioxane at 0° C. (reaction flask kept in an ice-water bath) was added 0.04 mL of piperidine. This mixture was subsequently stirred at 0° C. for 15 minutes and at room temperature for 11 hours. The product was isolated by diluting the mixture with 20 mL of 1:1 (v/v) 1M aqueous NaOH:saturated brine and extraction with ether. The combined extracts were washed thoroughly with 25 mL portions of 10% aqueous sodium chloride, then were dried over anhydrous magnesium sulfate and subsequently filtered. Removal of the ether by evaporation at reduced pressure afforded 1.89 g (98% yield) of crystalline cyanoester 3: mp 92°–93.5° C. [reported mp: 93°–94° C., lit. reference: F. D. Popp and A. Catala, *J. Org. Chem.*, 26, 2738 (1961)].

EXAMPLE IV

Preparation of (E)-Ethyl 2-Cyano-3-(3'-pyridyl)-2-propenoate (4)

A procedure described by B. C. McKusick, R. E. Heckert, T. L. Cairns, D. D. Coffman, and H. F. Mower [*J. Am. Chem. Soc.*, 80, 2806 (1958)] was used to prepare this compound. A mixture of 3.037 g (28.3 mmoles) of 3-pyridinecarboxaldehyde (commercially available: Aldrich Chemical Co.), 3.00 mL (28.2 mmoles) of ethyl cyanoacetate, 0.10 mL (1.01 mmole) of piperidine, and 0.25 mL of glacial acetic acid in 20 mL of absolute ethanol was heated at reflux for 2 hours, after which 40 mL of water was added to this hot solution and the mixture was allowed to cool gradually to room temperature. The crystalline cyanoester 4 was collected by filtration and washed twice with 10 mL-portions of 2:1 (v/v) water:ethanol. Yield of 4: 3.64 g (64%); mp 124°–125° C.

EXAMPLE V

Preparation of (E)-Ethyl 2-Cyano-5-methyl-2-hexenoate (5)

To a mixture of 3.00 mL (28.0 mmoles) of isovaleraldehyde and 3.00 mL (28.1 mmoles) of ethyl cyanoacetate in 4.0 mL of glacial acetic acid was added a solution of 0.10 mL of piperidine in 1.0 mL of glacial acetic acid. This mixture was subsequently stirred at room temperature for 18 hours, after which the product was isolated by diluting the mixture with 50 mL of 10% aqueous sodium chloride and extraction with ether. The combined extracts were washed thoroughly with 50 mL portions of 10% aqueous NaCl, followed by washes with 50 mL of 1:1 (v/v) 1M aqueous NaOH:saturated brine and saturated brine. The organic extracts were then dried over anhydrous magnesium sulfate and subsequently filtered. Removal of the ether by evaporation at reduced pressure, followed by distillation, afforded 3.91 g (77% yield) of cyanoester 5: bp 78°–90° C. (bath temperature, 0.07 mm).

EXAMPLE VI

Preparation of Diethyl Benzylidenemalonate (8)

A mixture containing 3.0 mL (19.8 mmoles) of diethyl malonate, 2.0 mL (19.6 mmoles) of benzaldehyde, 0.10 mL of piperidine, and 65 mg of benzoic acid in 35 mL of benzene was heated at reflux for 6 hours with continuous azeotropic removal of water by means of a Dean-Stark trap. Isolation of the product in the manner described in the procedure of Example I, followed by fractional distillation, afforded 4.27 g (88% yield) of diester 8: bp 105°–140° C. (bath temperature, 0.10 mm). Subsequent treatment of diester 8 with 2-nitropropane and sodium ethoxide in ethanol at reflux, as described for the corresponding cyanoester 1 in Example VIII, failed to yield a cyclopropanoid product.

EXAMPLE VII

Preparation of Ethyl(1-Methyl-4-piperidylidene)-cyanoacetate (9)

A mixture containing 1.05 g (9.27 mmoles) of 1-methyl-4-piperidone (commercially available: Aldrich Chemical Co., 1.00 mL (9.4 mmoles) of ethyl cyanoacetate, and 148 mg of ammonium acetate in 35 mL of benzene was heated at reflux for 3 hours with continuous azeotropic removal of water by means of a Dean-Stark trap. The product was isolated by cooling the mixture to room temperature, pouring it into 30 mL of 2:1 (v/v) 1M aqueous NaOH:saturated brine, and extraction with ether. The organic extracts were washed with 10% aqueous sodium chloride solution, then were dried over anhydrous sodium sulfate and subsequently filtered. Removal of the ether and benzene by evaporation at reduced pressure afforded 1.46 g (76% yield) of cyanoester 9.

EXAMPLE VIII

Preparation of Ethyl 1-Cyano-2,2-dimethyl-3-phenylcyclopropanecarboxylate (10)

A mixture of 534 mg (2.65 mmoles) of cyanoester 1 (produced in accordance with Example I), 0.25 mL (2.78 mmoles) of 2-nitropropane, and 4.0 mL (2.60 mmoles of sodium ethoxide) of an 0.65M solution of sodium ethoxide (prepared from sodium metal and ethyl alcohol) in ethyl alcohol was stirred at room temperature for 10 minutes and subsequently heated at gentle reflux, protected from atmospheric moisture, for 3 hours. The product was isolated by cooling the mixture to room temperature, diluting it with 30 mL of 10% aqueous sodium chloride, and extraction with dichloromethane. The dichloromethane extracts were washed with 10% aqueous sodium chloride, dried over anhydrous magnesium sulfate, and filtered. Removal of the dichloromethane at reduced pressure, followed by evaporative distillation, [bath temperature: 125°–135° C. (0.05 mm)], afforded 620 mg (96% yield) of cyclopropanoid cyanoester 10. The presence of a single sharp peak ($\delta 3.30$) for the cyclopropyl H in 10 suggested the presence of only one stereoisomer (neglecting optical isomerism)—the phenyl and cyano substituents being cis, as shown by subsequent decarbalkoxylation results).

EXAMPLE IX

Preparation of Methyl 1-Cyano-2,2-dimethyl-3-phenylcyclopropanecarboxylate (11)

A mixture of 511 mg (2.73 mmoles) of cyanoester 2 (produced in accordance with Example II), 0.25 mL (2.78 mmoles) of 2-nitropropane, and 2.64 mmoles of sodium methoxide (prepared from 61 mg of sodium and methyl alcohol) in 4.0 mL of absolute methanol was stirred at room temperature for 10 minutes and subsequently heated at reflux, protected from atmospheric moisture, for 7½ hours. The product was isolated as described in the procedure of Example VIII, affording 483 mg (77% yield) of cyclopropanoid cyanoester 11, stereochemically homogeneous as shown by NMR analysis: $\delta 3.83$ (singlet, $CO_2CH_3$) and $\delta 3.30$ (singlet, cyclopropyl H).

EXAMPLE X

Preparation of Ethyl 1-Cyano-2,2-dimethyl-3-(o-chlorophenyl)-cyclopropanecarboxylate (12)

A mixture of 640 mg (2.7 mmoles) of (E)-ethyl 2-cyano-3-(o-chlorophenyl)-2-propenoate (6) (prepared from ethyl cyanoacetate and o-chlorobenzaldehyde using the procedure described in Example I for an analogous cyanoester), 0.25 mL (2.78 mmoles) of 2-nitropropane, 357 mg (2.6 mmoles) of anhydrous potassium carbonate, and 4.0 mL of absolute ethyl alcohol was heated at reflux for 3 hours. The product was isolated as described in the procedure of Example VIII, affording 664 mg (88% yield) of cyclopropanoid cyanoester 12, stereochemically homogeneous as shown by NMR analysis: $\delta 3.22$ (singlet, cyclopropyl H); bp: 122°–155° C. (bath temperature, 0.08 mm).

EXAMPLE XI

Preparation of Ethyl 1-Cyano-2-(2'-thienyl)-3,3-dimethylcyclopropanecarboxylate (13)

A mixture of 557 mg (2.69 mmoles) of cyanoester 3 (produced in accordance with Example III), 0.25 mL (2.78 mmoles) of 2-nitropropane, and 4.0 mL of an 0.65M solution of sodium ethoxide (prepared from sodium metal and ethyl alcohol) in ethyl alcohol was heated at reflux, protected from atmospheric moisture, for 9 hours. The product was isolated as described in the procedure of Example VIII, affording 524 mg (78% yield) of cyclopropanoid cyanoester 13: bp 120°–148° C. (bath temperature, 0.05 mm); sterochemically homogeneous as shown by NMR analysis ($\delta 3.30$, singlet, cyclopropyl H).

EXAMPLE XII

Preparation of Ethyl 1-Cyano-2,2-dimethyl-3-isobutylcyclopropanecarboxylate (14)

A mixture of 490 mg (2.70 mmoles) of cyanoester 5 (produced in accordance with Example V), 0.25 mL (2.78 mmoles) of 2-nitropropane, and 4.0 mL of an 0.65M solution of sodium ethoxide (prepared from sodium metal and ethyl alcohol) in absolute ethyl alcohol was heated at reflux, protected from atmospheric moisture, for 3½ hours. The product was isolated as described in the procedure of Example VIII, affording 575 mg (95% yield) of cyclopropanoid cyanoester 14: bp 80°–102° C. (bath temperature, 0.05 mm).

EXAMPLE XIII

Preparation of Ethyl 1-Cyano-2,2-dimethyl-3-(p-methylphenyl)cyclopropanecarboxylate (15)

A mixture of 576 mg (2.68 mmoles) of (E)-ethyl 2-cyano-3-(p-methylphenyl)-2-propenoate (7) [prepared from ethyl cyanoacetate and p-tolualdehyde (p-methylbenzaldehyde) using the procedure described in Example I for an analogous cyanoester], 0.25 ml (2.78 mmoles) of 2-nitropropane, 398 mg (2.88 mmoles) of anhydrous potassium carbonate, and 2.0 ml of absolute ethanol was heated at reflux for 7 hours. The product was isolated as described in the procedure of Example VIII, affording 511 mg (74% yield) of cyclopropanoid cyanoester 15: bp: 155°–183° C. (bath temperature, 0.15 mm).

EXAMPLE XIV

Preparation of 2,2-Dimethyl-3-phenylcyclopropanecarbonitrile (17)

A mixture of 234 mg (0.96 mmole) of cyclopropanoid cyanoester 10 (produced in accordance with Example VIII), 174 mg (2.1 mmoles) of sodium bicarbonate, and 35 mg of water in 2.0 mL of 1,3-propanediol was heated at reflux, protected from atmospheric moisture, for 45 minutes. The product was isolated by diluting the cooled mixture with 25 mL of saturated brine and extraction with ether. The ether extracts were washed in successive order with 20 mL of 1:1 (v/v) 1M aqueous NaOH:saturated brine and 20 mL of 10% aqueous sodium chloride, dried over anhydrous magnesium sulfate, and filtered. Removal of the ether by evaporation at reduced pressure afforded 157 mg (95% yield) of nitrile 17 as a mixture of cis and trans stereoisomers, subsequently shown by NMR analysis (vinyl H absorption at approximately 5.0δ) to be accompanied by a minor amount (~10–15%) of ring-opened by-product.

EXAMPLE XV

Preparation of 1-Cyano-2,2-dimethyl-3-phenylcyclopropanecarboxylic Acid (18)

A mixture of 147 mg (0.60 mmole) of cyclopropanoid cyanoester 10 (produced in accordance with Example VIII), 88 mg (0.64 mmole) of anhydrous potassium carbonate, 0.50 mL of water, and 2.0 mL of methyl alcohol was heated at reflux for 20 minutes. The product was isolated by cooling the mixture to room temperature, cautiously acidifying it by addition of 2 mL of 2M aqueous HCl, subsequent dilution with 20 mL of saturated brine, and extraction with ether. The ether extracts were washed with saturated brine, then dried over anhydrous magnesium sulfate and subsequently filtered. Removal of the ether by evaporation at reduced pressure afforded 110 mg (85% yield) of cyanoacid 18, which was immediately decarboxylated in accordance with Example XVI.

EXAMPLE XVI

Preparation of cis and trans-2,2-Dimethyl-3-phenylcyclopropanecarbonitrile (17)

A mixture of 105 mg (0.49 mmol) of cyanoacid 18 (produced in accordance with Example XV), 85 mg (1.0 mmole) of NaHCO$_3$, 18 mg. of water, and 1.0 mL of 1,3-propanediol was heated at reflux, protected from atmospheric moisture, for 45 minutes. The product was isolated as described in the procedure of Example XIV, affording 66 mg (79% yield) of nitrile 17 as a mixture of cis and trans stereoisomers. In contrast to the product isolated in Example XIV, no ring-opened nitrile could be detected by NMR analysis. The trans stereoisomer was characterized by two singlets on its NMR spectrum at δ0.90 and 1.51 (two methyls), whereas the corresponding absorptions for the cis stereoisomer were δ1.17 and 1.35.

EXAMPLE XVII

Preparation of cis- and trans-2,2-Dimethyl-3-(p-methylphenyl)cyclopropanecarbonitrile (19)

A mixture of 222 mg (0.97 mmole) of cyanoacid 16 [prepared in quantitative yield from cyanoester 15 using the procedure described in Example XV for an analogous compound], 127 mg (1.5 mmoles) of sodium bicarbonate, 170 mg (4.0 mmoles) of lithium chloride, and 72 mg (4.0 mmoles) of water in 2.00 ml of dimethyl sulfoxide was heated at 165° C. (external oil bath temperature), while being protected from atmospheric moisture for 18 hours. The product was isolated as described in the procedure of Example XIV, affording 147 mg (82% yield) of nitrile 19 as a 1:1 mixture of cis and trans stereoisomers.

NOTE: Attempts to decarbalkoxylate (i.e., 15→19 directly) cyanoester 15 using the procedure described in Example XIV gave low yields of the desired product (19) and much ring-opened material. Alternatively, an attempt to decarboxylate (i.e., 16→19) cyanoacid 16 in 1,3-propanediol using a procedure similar to that described in Example XVI gave predominately the cis stereoisomer of nitrile 19.

EXAMPLE XVIII

Preparation of Ethyl 1'-Cyano-3',3'-dimethyl-spiro(4-methyl-4-azacyclohexane-1,2'-cyclopropane)-1'-carboxylate (20)

A mixture of 567 mg (2.72 mmoles) of cyanoester 9 (produced in accordance with Example VII), 0.25 mL (2.78 mmoles) of 2-nitropropane, and 4.0 mL of an 0.65M solution of sodium ethoxide (prepared from sodium metal and ethyl alcohol) in absolute ethyl alcohol was heated at reflux, protected from atmospheric moisture, for 5 hours. The product was isolated as described in the procedure of Example VIII, affording 485 mg (71% yield) of cyclopropanoid cyanoester 20: bp 120°–150° C. (bath temperature, 0.05 mm).

What is claimed:

1. A process for synthesis of a cyclopropanoid cyanoester comprising the following steps:
   (A) forming a reaction mixture in a $C_1$ through $C_4$ monohydric alcohol solvent of
      (i) 2-nitropropane, (ii) a cyanoester selected from the group consisting of

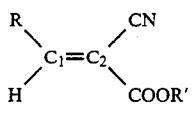
(a)

and

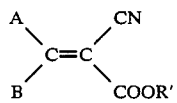
(b)

wherein R' is methyl or ethyl, A, B represents a group having the formula —$(CH_2)_n$— or —$(CH_2)_2$—Y—$(CH_2)_2$—, n=3, 4, or 5, Y being $NCH_3$, O, or S, and R can be selected from the class consisting of:
  (1) alkyl, haloalkyl, alkenyl, haloalkenyl, cycloalkyl, carboalkoxy, and cycloalkenyl groups having up to ten carbons;
  (2) a heterocyclic residue selected from the group consisting of furan, thiophene, pyridine, pyrrole and indole;
  (3) phenyl and naphthyl groups; and,
  (4) monosubstituted phenyl groups and disubstituted phenyl groups wherein the substituents are selected from the group consisting of alkyl, halogen, nitro, alkoxy, and haloalkyl;
  provided that when R is alkenyl, R is not conjugated with the double bond between $C_1$ and $C_2$ and when R is a substituted phenyl group, at least one of the ortho carbons of said phenyl group is bonded to hydrogen; and
(iii) a base selected from the group consisting of alkali metal alkoxides and alkali metal carbonates;
(B) heating said reaction mixture in refluxing alcohol solvent; and
(C) isolating a cyclopropanoid cyanoester from said reaction mixture.

2. The process of claim 1 wherein said alcohol solvent is selected from the group consisting of methanol and ethanol.

3. The process of claim 1 wherein said step of isolating a cyclopropanoid cyanoester comprises:
  (A) cooling said reaction mixture;
  (B) diluting said reaction mixture with aqueous sodium chloride;
  (C) extracting the diluted reaction mixture with dichloromethane; and,
  (D) evaporating said dichloromethane at reduced pressure.

4. The process of claim 1 wherein said cyanoester has the formula:

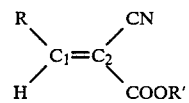

wherein R' is methyl or ethyl, and R can be selected from the class consisting of:
  (1) alkyl, haloalkyl, alkenyl, haloalkenyl, cycloalkyl, carboalkoxy, and cycloalkenyl groups having up to ten carbons;
  (2) a heterocyclic residue selected from the group consisting of furan, thiophene, pyridine, pyrrole and indole;
  (3) phenyl and naphthyl groups, and;
  (4) monosubstituted phenyl groups, and disubstituted phenyl groups wherein the substituents are selected from the group consisting of alkyl, halogen, nitro, alkoxy, and haloalkyl; provided that when R is alkenyl, R is not conjugated with the double bond between $C_1$ and $C_2$ and when R is a substituted phenyl group, at least one of the ortho carbons of said phenyl group is bonded to hydrogen.

5. The process of claim 1 wherein said cyanoester is ethyl(1-methyl-4-piperidylidene)-cyanoacetate.

6. The process of claim 1 wherein said cyanoester is (E)-ethyl 2-cyano-3-(o-chlorophenyl)-2-propenoate.

7. The process of claim 1 wherein said cyanoester is (E)-ethyl 2-cyano-3-(p-methylphenyl)-2-propenoate.

8. The process of claim 1 wherein said cyanoester is (E)-ethyl 2-cyano-3-(3'-pyridyl)-2-propenoate.

9. The process of claim 1 wherein said cyanoester is (E)-ethyl 2-cyano-5-methyl-2-hexenoate.

* * * * *